United States Patent [19]

Brenner

[11] 4,340,601

[45] Jul. 20, 1982

[54] DOPAMINERGIC ISOQUINOLINES

[75] Inventor: L. Martin Brenner, Havertown, Pa.

[73] Assignee: SmithKline Corporation, Philadelphia, Pa.

[21] Appl. No.: 166,933

[22] Filed: Jul. 8, 1980

[51] Int. Cl.$^3$ ..................... A61K 31/47; C07D 217/16

[52] U.S. Cl. ..................................... 424/258; 546/144

[58] Field of Search ......................... 546/144; 424/258

[56] References Cited

U.S. PATENT DOCUMENTS 2,813,872 11/1957 Schmutz .............................. 546/144

3,666,763 5/1972 Grethe et al. ........................ 546/144

3,823,148 7/1974 Jansen et al. ........................ 546/144

3,947,456 3/1976 Rheiner ............................... 546/144

4,042,697 8/1977 Garside et al. ...................... 424/258

*Primary Examiner*—Donald G. Daus

*Assistant Examiner*—James H. Turnipseed

*Attorney, Agent, or Firm*—William H. Edgerton; Richard D. Foggio; Alan D. Lourie

[57] ABSTRACT

A new series of compounds having renal vasodilating activity described. The compounds are 2-allyl-8-halo-4-(p-hydroxyphenyl)-1,2,3,4-tetrahydroisoquinolines.

7 Claims, No Drawings

DOPAMINERGIC ISOQUINOLINES

This invention comprises a group of new chemical compounds which are 2-allyl-8-halo-4-(p-hydroxyphenyl)-1,2,3,4-tetrahydroisoquinolines. These compounds increase blood flow in the kidney by decreasing vascular resistance by means of a dopaminergic effect on peripheral dopamine receptors. As such they are useful as antihypertensive agents.

DESCRIPTION OF THE PRIOR ART

A number of 1-phenyl-2,3,4,5-tetrahydro-1H-3-benzazepines have been described which have renal dopaminergic activity such as U.S. Pat. No. 4,197,297. These prior art compounds have a different ring system from those of the present invention.

DESCRIPTION OF THE INVENTION

The compounds of this invention have structures characterized by a 1,2,3,4-tetrahydroisoquinoline nucleus substituted by a halo at position 8, two hydroxy groups at positions 6 and 7, a hydroxyphenyl at position 4 and an allyl at position 2. The compounds therefore may be represented by the following structural formula:

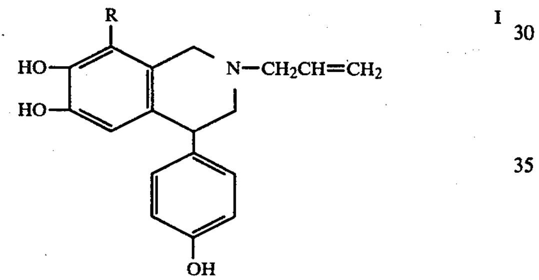

in which R is halo that is chloro, bromo, fluoro or iodo. Advantageously, R is chloro.

The three phenolic groups may also be derivatized by forming tri-lower alkanoyl esters. Each of the lower alkanoyl groups have from 2–7 carbon atoms. For convenience in preparation, the same alkanoyl group is used at each position.

The pharmaceutically acceptable acid addition salts having the utility of the free bases of Formula I, prepared by methods well known to the art, are formed with both inorganic and organic acids, for example: maleic, fumaric, succinic, methane sulfonic, ethanedisulfonic, acetic, oxalic, propionic, tartaric, salicylic, citric, gluconic, aspartic, itaconic, benzene sulfonic, hydrochloric, hydrobromic, sulfuric, phosphoric and nitric acids. The hydrohalic and especially methane sulfonic acid salts are of particular utility.

The compounds of this invention are prepared by the following sequence of reactions:

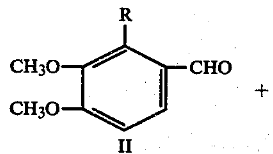

+

-continued

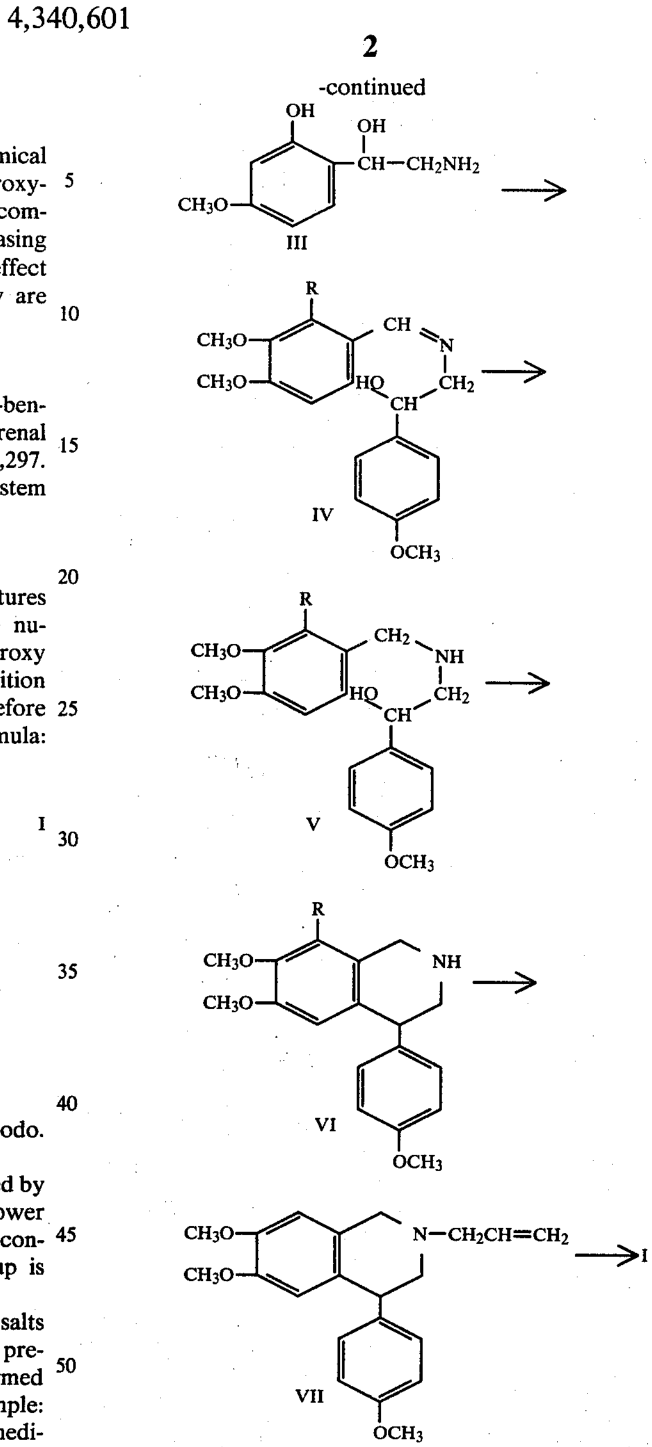

Details of this reaction sequence are described in the examplary material presented below. Other variations of the reaction sequence or indeed other synthetic paths to the final products will be apparent to those skilled in the art. Other O-protecting groups are useful such as benzyl, other lower alkyl groups for example ethyl, propyl, or for 6,7-hydroxy groups together, methylene or ethylene. Also other common reducing agents are used for the reduction of the imine intermediate (IV) such as lithium aluminum hydride or sodium cyanoborohydride. Alternative cyclizing groups known to the art give good yields of the useful trialkoxytetrahydroisoquinoline intermediate (VI). In the reaction sequence outlined above R is halo.

Of particular interest is the final step of the reaction sequence (VII→I) in which a 2-allyl-8-halo-6,7-dimethoxy-4-(p-methoxyphenyl)-1,2,3,4-tetrahydroisoquinoline base or one of its acid addition salts is reacted with an ether cleaving agent which will not react with the functional group of the allyl substituent. The reaction readily proceeds with boron tribromide or boron trichloride in a halogenated organic solvent such as methylene chloride, carbon tetrachloride or chloroform. An alternative ether cleaving agent is trifluoromethylsulfonic acid in thioanisole. The product is isolated by methods known to the art.

The renal dopaminergic activity of the compounds of this invention was demonstrated by monitoring mean arterial blood pressure (MAP), mean renal blood flow (RBF), renal vascular resistance (RVR) and heart rate (HR) in a normal anesthetized dog in a standard pharmacological procedure. The selected compound is administered by intravenous infusion and is expressed as μg/kg/min. Each dose is infused for five minutes. A clinically useful compound, dopamine, was run as a positive control.

Compound A: 2-Allyl-8-chloro-6,7-dihydroxy-4-(p-hydroxyphenyl)-1,2,3,4-tetrahydroisoquinoline hydrobromide:

| | | % Change in 2 Dogs | | | |
|---|---|---|---|---|---|
| | Dose | MAP | RBF | RVR | HR |
| Dopamine | 3 | −3.3 | +35.3* | −28.2 | 0 |
| A | 3 | 0 | −9.3* | +10.6* | +1.8 |
| | 30 | −4.5 | +19.4* | −19.0* | −2.5 |
| | 300 | 0 | −12.9* | +14.8* | +7.8* |

*statistically significant

The test compound demonstrates good renal vasodilation of the dopaminergic type at 30 μg/kg/min.

Compound A also has diuretic activity. In doses of 30 mg/kg orally (as the base) in fasted rats with a water-salt load and vasopressin, the compound demonstrated significant increase in urine volume, sodium ion excretion and decrease in urine osmolality.

The pharmacodynamic methods of this invention comprise administration of an active nontoxic quantity of a compound of Formula I, one of its pharmaceutically acceptable acid addition salts or one of its O-lower alkanoyl esters internally, preferably either orally or parenterally, to a human or animal patient in need of renal vasodilation or diuresis. The primary desired effect on the kidney is to decrease vascular resistance and increase blood flow. The effect is similar to the renal effects of dopamine and like clinical effects may be thereby realized such as in treating hypertension or other abnormal cardiovascular conditions. The route of administration may be any that effectively transports the active ingredient to the renal receptors but oral, rectal, intravenous or subcutaneous routes of administration are conveniently used. The compound of Formula I is administered in a nontoxic quantity sufficient to induce renal vasodilation. Most conveniently the active ingredient is combined with a pharmaceutical carrier and administered to the patient from 1–5 times daily as necessary to effect the desired pharmacodynamic result. The daily dosage is based on total quantities of the base of from about 150 mg to about 1 g per day, administered preferably as 75–350 mg of base per dosage unit which is administered from 1–5 times daily orally. The parenteral dosage regimen would be lower than the oral regimen. The daily dosage regimen is selected with the conditions known to be factors in the art, for example, the age and weight of the subject, the severity of the clinical disorder, the route of administration and the relative potency of the active ingredient compared to the activity of dopamine in the test systems described hereinbefore. When the method of this invention is carried out renal vasodilation similar to that induced by dopamine is realized.

The pharmaceutical compositions of this invention having renal dilating activity which are of use for treating hypotensive patients are prepared in conventional dosage unit forms by incorporating a compound of Formula I, or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably, the compositions will contain the active ingredient in an active but nontoxic amount selected from about 50 mg to about 500 mg preferably about 75–350 mg of active ingredient calculated as the base per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatin capsules. Similarly, the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed ranging from rectal suppositories to sterile solutions for parenteral or injectable use. Thus, if a solid carrier for oral administration is used the preparation can be tableted, placed in a hard gelatin capsule in powder, regular or sustained release pellet or tablet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The following examples are designed to teach the practice of the invention but not to limit its scope. All temperatures are Centigrade.

EXAMPLE 1

A mixture of 8.0 g (0.04 m) of 2-chloro-3,4-dimethoxybenzaldehyde (II, R=Cl), 9.1 g (0.04 m) of 2-amino-1-(4-methoxyphenyl)ethanol (III), 5.5 ml (0.04 m) of triethylamine and 40 ml of methanol was heated on a steam bath to boiling then stirred at ambient temperature. After cooling the desired Schiff base (IV) was recovered by filtration; 13.0 g (93%), m.p. 130°–131°. The Schiff base (12.0 g, 0.03 m) was suspended in 75 ml of methanol to which 1.0 g (0.03 m) of sodium borohydride was added with stirring. Stirring was continued overnight. The solid was then recovered to give 9.75 g of product while 0.65 g was recovered from the mother liquor; total yield 10.4 g (87%), m.p. 119°-120° of N-(2-chloro-3,4-dimethoxybenzyl)-1-(4-methoxyphenyl)-2-aminoethanol (V).

A mixture of 10.4 g (0.03 m) of aminoethanol, 100 ml of trifluoroacetic acid and 2.5 ml of concentrated sulfuric acid was heated at reflux for 3 hours. The excess trifluoroacetic acid was evaporated. The residue was quenched with ice and water, then chloroform was added. The mixture was made basic with 40% sodium hydroxide. After extensive extraction with chloroform, the combined organic extracts were backwashed until neutral with water, brine then dried. Evaporation gave 9.3 g (93%) of a yellow oil, 8-chloro-6,7-dimethoxy-4-(p-methoxyphenyl)-1,2,3,4-tetrahydroisoquinoline (VI). This oil (800 mg) was dissolved in ether and treated with ethereal hydrogen chloride to give the hydrochloride salt, mp. 215°-216°.

A mixture of 6.5 g (0.019 m) of the trimethoxy base, 5.5 ml of triethylamine, 2.8 ml (0.021 m) of allyl bromide and 100 ml of acetonitrile was heated on the steam bath at 85°-95° for 3 hours. The solvent was evaporated. Water and ethyl acetate was added to the residue. The organic extract was washed with water, brine then dried. Evaporation gave 6.8 g (96%) of yellow oil. The material was purified over a silica gel column in chloroform-methanol (Rf~0.45). This material (400 mg) in ether was treated with ethereal hydrogen chloride to give 140 mg of the hydrochloride salt of 2-allyl-8-chloro-6,7-dimethoxy-4-(p-methoxyphenyl)-1,2,3,4-tetrahydroisoquinoline (VII), m.p. 149°-153°.

The N-allyl trimethoxy base (VII) (2.4 g, 0.0064 m) was dissolved in 50 ml of methylene chloride and mixed with a solution of 6.0 ml (0.64 m) of boron tribromide in 40 ml of methylene chloride at −15°. After stirring for 2 hours at room temperature, the mixture was cooled and quenched with methanol several times, the last time with 4 drops of 48% hydrogen bromide added. Final evaporation gave a foam which was dissolved in ethyl acetate-methanol. The mixture was heated at reflux briefly then cooled to give 1.5 g (52%) of 2-allyl-8-chloro-6,7-dihydroxy-4-(p-hydroxyphenyl)-1,2,3,4-tetrahydroisoquinoline hydrobromide, m.p. 252°-254° (d.).

Anal. Calcd. for $C_{18}H_{18}ClNO_3.HBr$: C, 52.38; H, 4.64; N; 3.39. Found: C, 52.32; H, 4.53; N, 3.39.

The above product (100 mg of base in salt form) is mixed with 275 mg of lactose and 2 mg of magnesium stearate then filled into a hard gelatin capsule which is administered orally to a patient in need of renal dilatation three times daily.

The hydrobromide salt (500 mg) is shaken with a mixture of ether-50% sodium carbonate solution. The ether layer is dried and divided into three aliquots. Reaction with methane sulfonic acid in ethanol, sulfuric acid in ether or evaporation gives the methane sulfonic acid salt, the sulfate and the base forms respectively.

EXAMPLE 2

Substituting stoichiometric quantities of 2-fluoro-3,4-dimethoxybenzaldehyde or 2-iodo-3,4-dimethoxybenzaldehyde in the chemical procedures of Example 1 gives first 2-allyl-8-fluoro-6,7-dimethoxy-4-(p-methoxyphenyl)-1,2,3,4-tetrahydroisoquinoline and 2-allyl-8-iodo-6,7-dimethoxy-4-(p-methoxyphenyl)-1,2,3,4-tetrahydroisoquinoline then upon treatment with boron tribromide in methylene chloride, 2-allyl-8-fluoro-6,7-dihydroxy-4-(p-hydroxyphenyl)-1,2,3,4-tetrahydroisoquinoline hydrobromide and 2-allyl-8-iodo-6,7-dihydroxy-4-(p-hydroxyphenyl)-1,2,3,4-tetrahydroisoquinoline hydrobromide.

The first (100 mg) in capsule form is given orally to a hypertensive patient four times daily. The second (125 mg) in capsule form is given orally to a patient in need of water diuresis four times daily.

EXAMPLE 3

A mixture of 1 g of 2-allyl-8-chloro-6,7-dihydroxy-4-(p-hydroxyphenyl)-1,2,3,4-tetrahydroisoquinoline hydrobromide, 1.3 ml of acetyl bromide and 200 ml of trifluoroacetic acid is stirred at 10° for 2 hours. After evaporation to dryness, the residue is purified, if necessary, by recrystallization to give 2-allyl-8-chloro-6,7-diacetoxy-4-(p-acetoxyphenyl)-1,2,3,4-tetrahydroisoquinoline hydrobromide. Similarly triisobutyryloxy, -propionyloxy, -isovaleryloxy, -n-butyryloxy and -n-heptanoyloxy ester derivatives are prepared.

What is claimed is:

1. A compound of the structure:

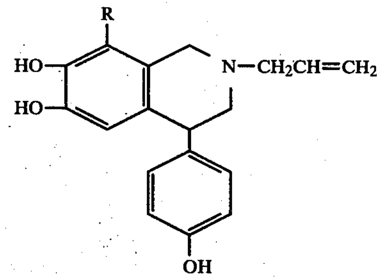

in which R is halo; tri-O-lower alkanoyl esters or pharmaceutically acceptable acid addition salts thereof.

2. The compound of claim 1 being 2-allyl-8-chloro-6,7-dihydroxy-4-(p-hydroxyphenyl)-1,2,3,4-tetrahydroisoquinoline hydrobromide.

3. The compound of claim 1 being 2-allyl-8-chloro-6,7-dihydroxy-4-(p-hydroxyphenyl)-1,2,3,4-tetrahydroisoquinoline methane sulfonic acid salt.

4. The compound of claim 1 being 2-allyl-8-chloro-6,7-dihydroxy-4-(p-hydroxyphenyl)-1,2,3,4-tetrahydroisoquinoline as the free base.

5. The compound of claim 1 being 2-allyl-8-iodo-6,7-dihydroxy-4-(p-hydroxyphenyl)-1,2,3,4-tetrahydroisoquinoline or one of its pharmaceutically acceptable acid addition salts.

6. The method of producing renal vasodilation in a patient in need thereof comprising administering orally or parenterally an effective nontoxic quantity of a compound of any one of claims 1, 2, 3, 4 or 5.

7. A pharmaceutical composition in dosage unit form having renal dilating activity comprising a nontoxic, effective quantity of a compound of any one of claims 1, 2, 3, 4 or 5 combined with a pharmaceutical carrier.

* * * * *